(12) United States Patent
Edwards et al.

(10) Patent No.: US 8,527,044 B2
(45) Date of Patent: Sep. 3, 2013

(54) USER INTERFACE METHOD AND APPARATUS FOR A MEDICAL DEVICE

(75) Inventors: D. Craig Edwards, Fall City, WA (US); Kelly J. Locke, Woodinville, WA (US); Mark Gausman, Bellevue, WA (US); Alex Otman, Bothell, WA (US); Richard C. Nova, Kirkland, WA (US); Shawn R. Bertagnole, Lake Stevens, WA (US)

(73) Assignee: Physio-Control, Inc., Redmond, WA (US)

( * ) Notice: Subject to any disclaimer, the term of this patent is extended or adjusted under 35 U.S.C. 154(b) by 1691 days.

(21) Appl. No.: 10/147,241

(22) Filed: May 15, 2002

(65) Prior Publication Data

US 2003/0216785 A1 Nov. 20, 2003

(51) Int. Cl.
*A61N 1/39* (2006.01)

(52) U.S. Cl.
USPC ............................................................ 607/5

(58) Field of Classification Search
USPC .......................................... 607/5–8, 4, 9, 10
See application file for complete search history.

(56) References Cited

U.S. PATENT DOCUMENTS

| | | | |
|---|---|---|---|
| 4,077,413 A | | 3/1978 | Partridge |
| 4,610,254 A | | 9/1986 | Morgan et al. |
| 4,619,265 A | | 10/1986 | Morgan et al. |
| 5,207,303 A | | 5/1993 | Oswalt et al. |
| 5,645,571 A | * | 7/1997 | Olson et al. .......................... 607/5 |
| 5,697,955 A | | 12/1997 | Stolte |
| 5,797,969 A | | 8/1998 | Olson et al. |
| 5,993,219 A | * | 11/1999 | Bishay ............................ 434/265 |
| 6,083,246 A | * | 7/2000 | Stendahl et al. ................... 607/5 |
| 6,125,298 A | * | 9/2000 | Olson et al. ........................ 607/5 |
| 6,125,299 A | | 9/2000 | Groenke et al. |
| 6,334,070 B1 | * | 12/2001 | Nova et al. ......................... 607/5 |
| 6,611,709 B2 | * | 8/2003 | Faller et al. ........................ 607/5 |
| 6,675,051 B2 | * | 1/2004 | Janae et al. ..................... 607/142 |
| 6,782,293 B2 | * | 8/2004 | Dupelle et al. ................. 607/142 |
| 6,872,080 B2 | * | 3/2005 | Pastrick et al. ................ 434/262 |
| 2003/0023274 A1 | * | 1/2003 | Chesley et al. ..................... 607/5 |
| 2003/0055458 A1 | * | 3/2003 | Hamilton et al. ................... 607/5 |
| 2003/0088276 A1 | * | 5/2003 | Covey et al. ....................... 607/5 |

FOREIGN PATENT DOCUMENTS

| | | |
|---|---|---|
| EP | 0 557 060 A2 | 8/1993 |
| WO | WO 01/85566 A1 | 11/2001 |

OTHER PUBLICATIONS

Physio-Control's LIFEPAK® 2 Portable Battery Operated Defibrillator and Cardioscope product information published prior to May 15, 2001.

(Continued)

*Primary Examiner* — Rex R Holmes

(74) *Attorney, Agent, or Firm* — Marger Johnson & McCollom PC

(57) ABSTRACT

A user interface method and apparatus is described for use with a defibrillator (100) such as an automated external defibrillator (AED). The user interface comprises a plurality of layered user interface components which become available to the operator of the defibrillator (100) as they become necessary or appropriate during the operation of the defibrillator (100) and treatment of the patient. In one embodiment, the layered user interface components comprise an on/off actuator (108), a lid (104), an electrode package (120) containing defibrillation electrodes (142, 144), and a shock key (170), as well as accompanying visual and aural instructions for operating the defibrillator (100) and for treating the patient.

26 Claims, 12 Drawing Sheets

(56) References Cited

OTHER PUBLICATIONS

Physio-Control's LIFEPAK® 3 Portable Battery Operated Cardioscope/Defibrillator product information published prior to May 15, 2001.

Physio-Control's LIFEPAK® 4 Portable Battery Operated Cardioscope/Defibrillator with ECG Recorder product information published prior to May 15, 2001.

Physio-Control's LIFEPAK® 100 Automatic Advisory Defibrillator User Guide, 1986.

Zoll AEDPLUS Administrator's Guide published at least as early as Jun. 10, 2002. Based on information and belief, the Zoll AEDPLUS defibrillator was offered for sale in the United States at least as early as Sep. 24, 2001.

\* cited by examiner

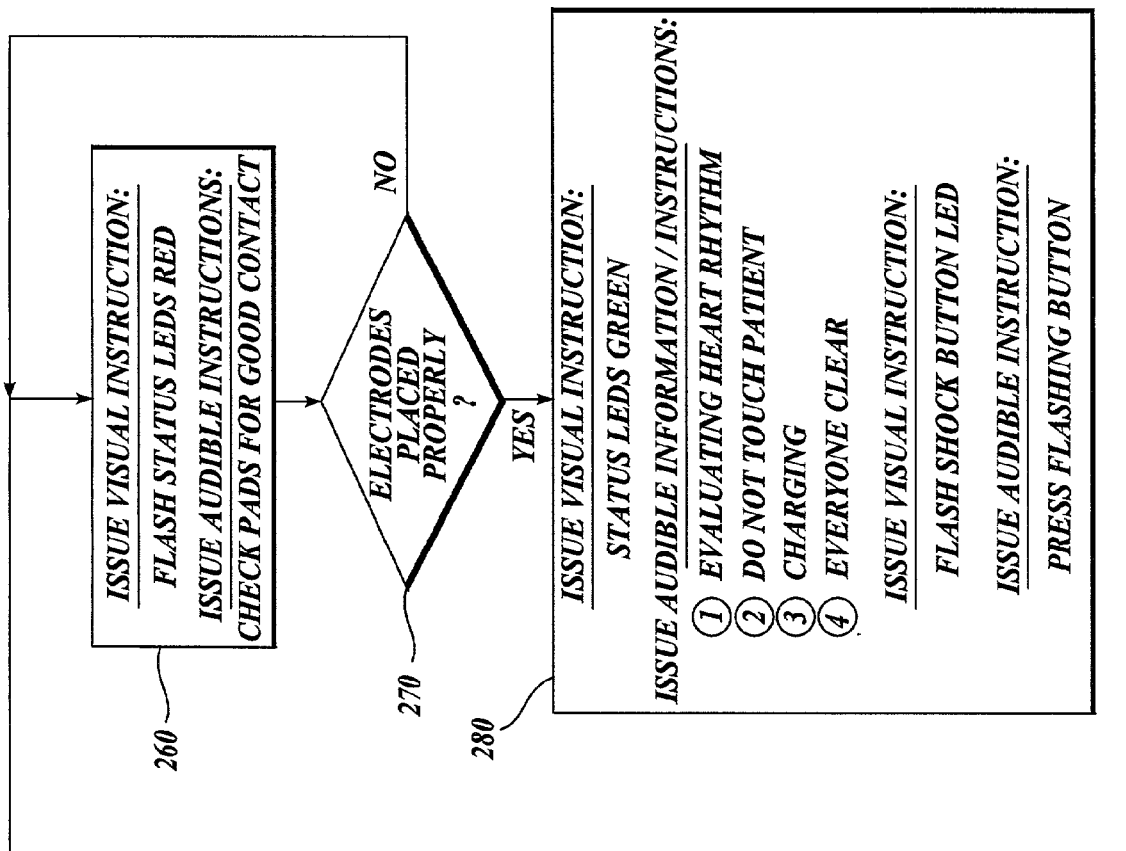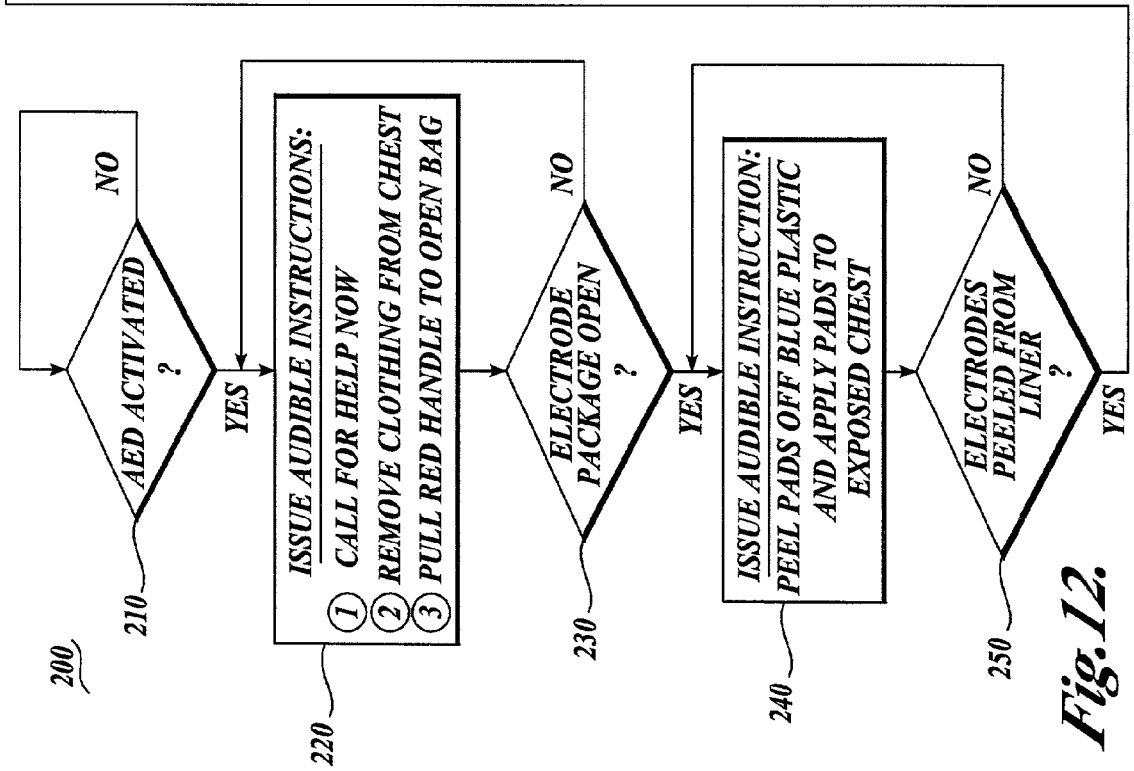
Fig. 12.

USER INTERFACE METHOD AND APPARATUS FOR A MEDICAL DEVICE

FIELD OF THE INVENTION

The present invention relates generally to a user interface method and apparatus for a medical device, and more particularly to a user interface method and apparatus for a defibrillator.

BACKGROUND OF THE INVENTION

Sudden cardiac death is the leading cause of death in the United States. Most sudden cardiac deaths are caused by ventricular fibrillation, in which the heart's muscle fibers contract without coordination, thereby interrupting normal blood flow into the body. The best known effective treatment for ventricular fibrillation is electrical defibrillation, in which an electrical pulse is applied to the patient's heart. The electrical pulse must be delivered within a short time after onset of ventricular fibrillation in order for the patient to have any reasonable chance of survival.

The current trend in the medical industry is to make life-saving portable medical devices, such as automated external defibrillators (AEDs), more widely accessible so that patients in need can be treated as quickly as possible. As the availability of portable medical devices continues to increase, more places will have these devices for use in emergency situations, such as in homes, police cars, worksites, and public gathering places. This increase also comes with the heightened likelihood that these portable medical devices will be used by people without medical training or people who are minimally trained in the handling of the medical devices. At the same time, the benefit of having life-saving medical devices immediately available in many places is not fully realized unless the medical devices can be promptly activated and used quickly in case of emergency. Therefore, a portable medical device, such as an AED, must be configured such that even a lay person can intuitively and quickly activate and use the medical device.

A medical device may automatically instruct an operator how to properly operate the medical device via various user interface components. For example, an AED may include a voice command system, a screen command system, and/or various graphics visible to the operator. Additional user interface components may also be available. For example, an AED typically includes a pair of defibrillation electrodes to be applied by an operator on the patient's body. Ideally, various user interface components should be immediately available to the operator of a medical device so that the operator can access or follow instructions offered by the user interface components to operate the medical device to save the patient's life. At the same time, some of the user interface components should be made available to the operator at the appropriate points during treatment of the patient in order to ensure that an instructional command, for example a voice prompt, of the medical device can timely guide the operator how to properly operate the device and treat the patient. This feature can be particularly helpful when the medical device is likely to be used by a lay person who is not very familiar with the medical device and thus needs to rely on commands issued by the medical device to properly handle the medical device.

SUMMARY OF THE INVENTION

In accordance with the present invention, a method and apparatus is disclosed for providing a layered user interface for an operator of a portable medical device, meaning that instructions concerning a series of operations to be performed by the operator for the treatment of a patient using the medical device, along with user interface tools to perform those operations, are provided to the operator as each of the operations becomes necessary or appropriate for treatment.

In one aspect of the invention, the medical device is a defibrillator, and a layered user interface is provided that includes an activation layer, an electrode application layer, and a defibrillation pulse delivery layer. The activation layer guides the operator to activate the defibrillator, and may include an on/off button. An on/off button is an example of an activator or activation device used by an operator to activate a medical device. The electrode application layer is made available to the operator subsequent to the activation layer, and guides the operator to apply electrodes to the patient. The electrode application layer may include an electrode package containing the electrodes, which are an example of a connector used by an operator to connect a medical device to a patient, and instructions concerning opening the package and applying the electrodes to the patient. The instructions concerning opening the package and applying the electrodes to the patient are examples of connection instructions concerning operator use of a connector. The defibrillation pulse delivery layer is made available to the operator subsequent to the electrode application layer, and guides the operator through delivery of a defibrillation pulse to the patient. The defibrillation pulse delivery layer may include a shock key that the operator presses to initiate delivery of the defibrillation pulse, and instructions concerning actuating the shock key. A shock key is an example of an initiator used by an operator to initiate treatment of a patient by a medical device.

In another aspect of the invention, a method for providing a user interface to an operator of an external defibrillator includes first drawing the attention of the operator to an actuator for activating the defibrillator. Upon the defibrillator being activated, an electrode package containing defibrillation electrodes is revealed to the operator, along with instructions for deploying the electrode package. Upon the electrode package being deployed, a shock key is revealed to the operator, along with instructions for actuating the shock key to initiate delivery of a defibrillation pulse. The various provided instructions may include visual, audible, written, or diagrammatic instructions.

In a further aspect of the invention, a method for providing a user interface to an operator of an external defibrillator includes first instructing the operator concerning activating the defibrillator. Instructing the operator concerning activating the defibrillator may include providing activation instructions concerning operator use of an activator or activation device, e.g., an on/off button. Once the defibrillator is activated, the operator is provided with an electrode package having an opener that is actuatable by the operator. The operator is instructed concerning opening the electrode package, and upon the operator opening the electrode package, the operator is instructed concerning removal of electrodes from the electrode package. Upon the operator removing the electrodes from the electrode package, the operator is instructed concerning the positioning of the electrodes on the patient. Upon the operator positioning the electrodes on the patient, the operator is instructed concerning subsequent care giving operations. In various aspects of the invention, the series of instructions provided to the operator includes written information, audible information, or color and diagrams relating to the successive operations to be performed by the operator of the defibrillator. The operator may also be provided with status information concerning the positioning of the electrodes on the patient, such as by providing the operator with visual status signals or with audible instructions prompting the operator to check the positioning of the electrodes.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 12 is a flow diagram depicting a prompting routine executed by the defibrillator to deliver visual and aural instructions to the operator.

DETAILED DESCRIPTION OF THE PRESENT INVENTION

In accordance with the present invention, a user interface is provided for a portable medical device comprising a plurality of layered user interface components. The user interface components are layered so as to become available to the operator of the device as they become necessary or appropriate during the operation of the device and treatment of the patient. Stated another way, the user interface components are layered to successively provide the operator with instructions and implements for operating the device and treating the patient. In the present description, the term "user interface component" is used to encompass any message and or/instruction sent to or received from the operator of the medical device, any device component or accessory used to send or receive such messages/instructions, and any implement that is physically used by the operator for operation of the device or treatment of the patient.

Figure 1:
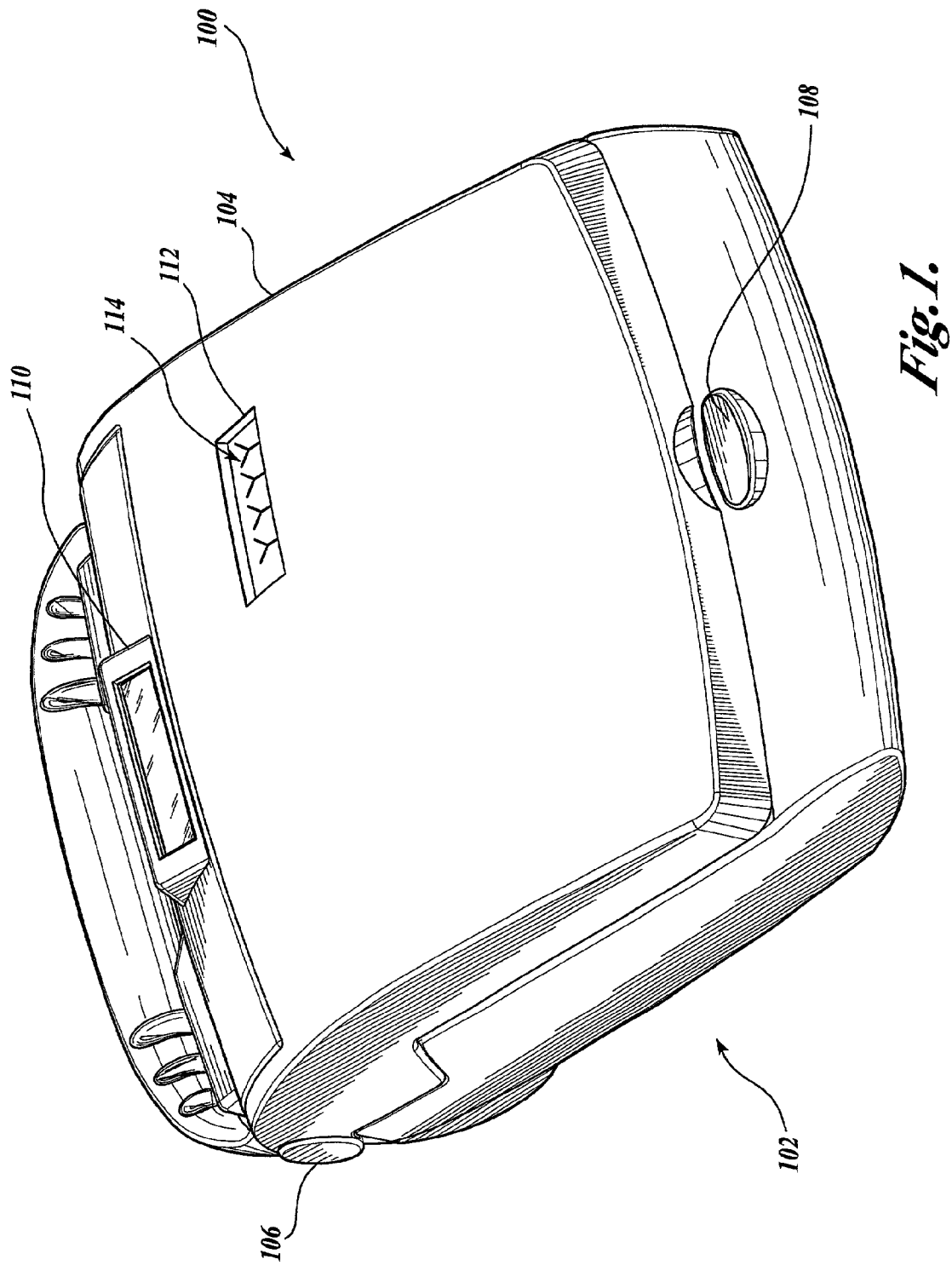
FIG. 1 is a perspective view of a medical device comprising a defibrillator which incorporates a layered user interface in accordance with the present invention.

FIG. 1 illustrates a medical device embodied as a portable automated external defibrillator (AED) 100, suitable for incorporating the layered user interface of the present invention. Although a defibrillator is used to describe this embodiment, in light of this disclosure, those skilled in the art will be able to implement the present invention with other types of medical equipment without undue experimentation. Further, in the following description certain specific details are set forth in order to provide a thorough understanding of various embodiments of the present invention. One skilled in the art will understand, however, that the present invention may be practiced without these details. In other instances, well-known functions, features, and operations of AEDs have not been shown or described in detail in order to avoid unnecessarily obscuring the description of the various embodiments of the present invention.

Returning to FIG. 1, an AED 100 incorporating a layered user interface formed in accordance with the present invention is depicted. As depicted in the illustrated embodiment, the user interface components of the layered user interface may comprise an on/off actuator 108, a lid 104, an electrode package 120 (see FIG. 3) and a shock key 170 (see FIG. 6), as well as accompanying visual and/or audible instructions for operating the AED and for treating the patient. As will be appreciated from the following description, beginning with the on/off actuator 108, each successive user interface component will become available to the operator as it becomes necessary for use by or instruction to the operator.

Figure 2:
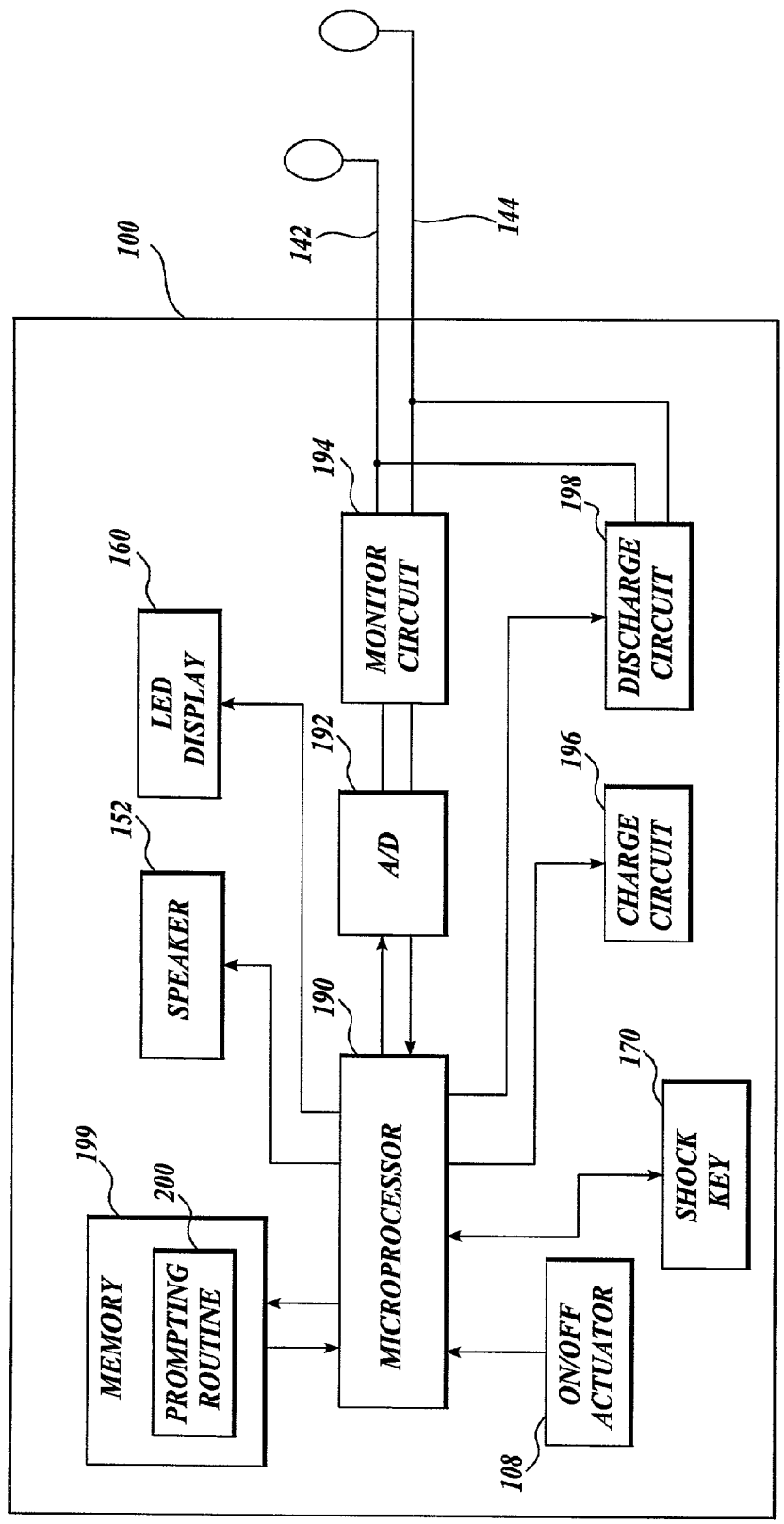
FIG. 2 is a schematic block diagram of several of the key components of the defibrillator shown in FIG. 1.

As shown in FIG. 1, the AED 100 includes a housing 102 containing the electronics necessary for the operation of the AED 100, as will be described in more detail below. As shown in more detail in FIG. 2, the AED 100 includes a microprocessor 190 which controls the operation of the AED 100. The microprocessor 190 is connected to an LED display 160, a speaker 152, an on/off actuator 108, and a shock key 170. The microprocessor 190 is also connected to a memory 199 which stores a prompting routine 200 (see FIG. 12) formed in accordance with the present invention to generate visual instructions upon the display 160 and any accompanying aural instructions transmitted via the speaker 152. In yet other embodiments of the present invention, the memory stores a voice recognition software module which allows the rescuer to operate the AED 100 and respond to visual and/or aural instructions via voice command rather than using the start and shock buttons. Such a module in combination with a microphone would then provide the rescuer with hands-free operation of the AED 100.

During defibrillation operation, the microprocessor 190 analyzes an electrocardiogram (ECG) of a patient using an automatic heart rhythm detection algorithm also stored in the memory 199 to identify whether the patient is experiencing a shockable heart rhythm, such as ventricular fibrillation. The detection algorithm executed by the microprocessor 190 in the actual embodiment of the present invention described herein is similar to that used in the LIFEPAK® 500 defibrillator provided by Medtronic Physio-Control Corp. of Redmond, Wash. Other known heart rhythm detection algorithms may also be used without departing from the scope of the present invention, such as those algorithms designed to comply with standards promulgated by the Association for the Advancement of Medical Instruments (AAMI). The ECG signals analyzed by the detection algorithm are collected by defibrillation electrodes 142, 144 and passed through a monitor circuit 194 to an analog-to-digital converter 192. The analog-to-digital converter 192 then passes the digitized signals to the microprocessor 190. If the microprocessor 190 detects a shockable rhythm, the microprocessor causes a charge circuit 196 to generate a current causing a storage capacitor (not shown) to charge in preparation for delivery of a defibrillation pulse. When the capacitor is fully charged, and delivery of the defibrillation pulse initiated, a discharge circuit 198 coupled to the microprocessor 190 and charge circuit 196 discharges the defibrillation pulse to the defibrillation electrodes 142, 144 for application of the defibrillation pulse to the patient.

Figure 3:
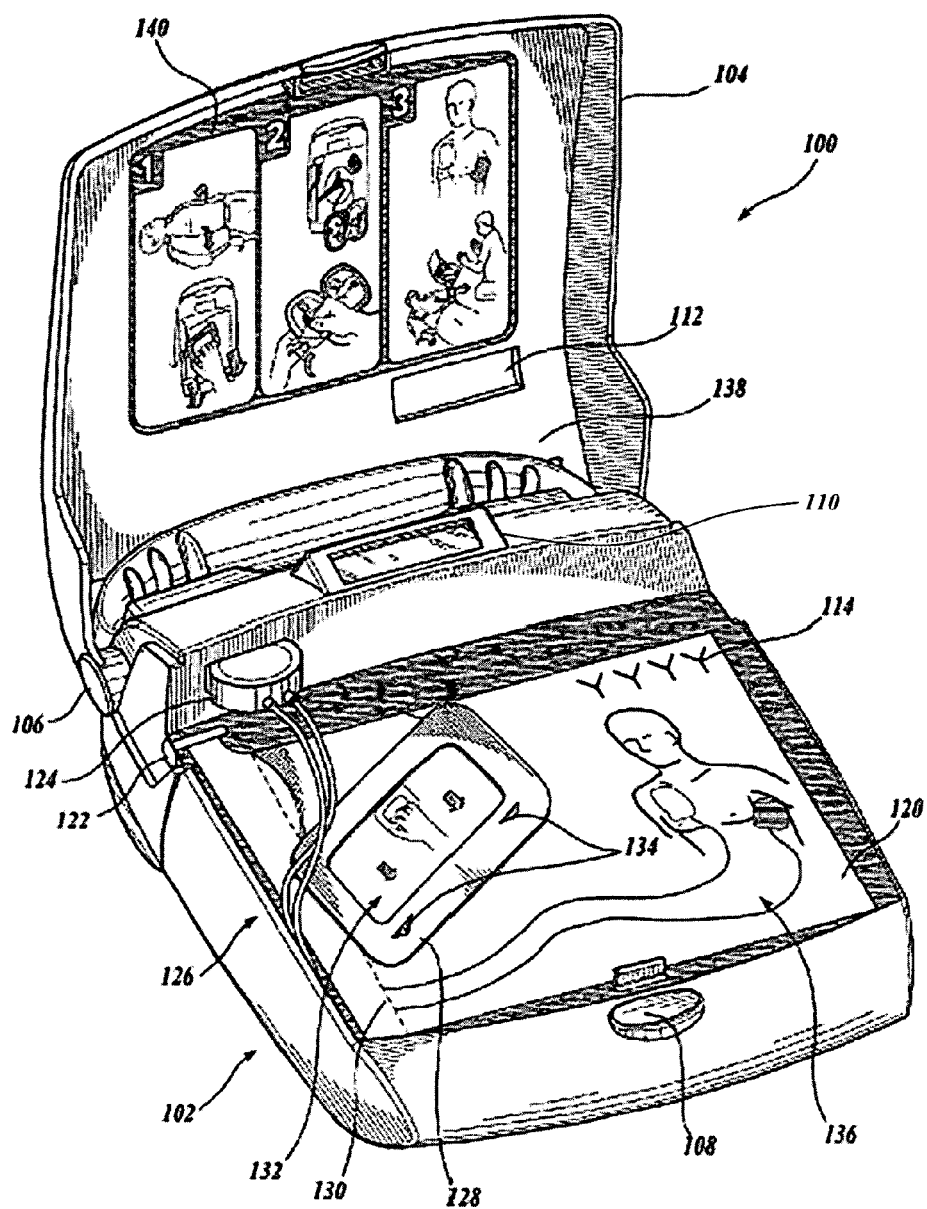
FIG. 3 depicts the defibrillator of FIG. 1 wherein a lid of the defibrillator is opened, revealing an electrode package having a handle previously hidden beneath the lid.

Returning to FIG. 1, the AED housing 102 includes an on/off actuator 108 which is sized and colored so as to attract the operator's attention as the first action required to use the AED 100. For example, in one embodiment, the on/off actuator 108 is large in size (relative to its required mechanical function) and colored bright yellow to visually contrast with the substantially gray/black colored lid 104 of the AED 100. Though the on/off actuator 108 is illustrated to be in the form a button, the actuator may take various other shapes and forms, for example, a membrane, plate, bar, etc., as long as it is adapted to receive an operator's instruction to activate the AED 100. In one embodiment, the on/off actuator 108 is configured so that depressing it sequentially activates the AED 100 and opens the next user interface component, i.e., a lid 104. The lid 104 is pivotally coupled to the housing 102 at two pivot points 106 in a conventional manner, so that the lid 104 can be opened as shown in FIG. 3. Alternatively, movement of the lid 104 to an open position can be the event activating the AED 100. Indeed, one skilled in the art will appreciate that the presence of the on/off actuator 108 is optional, and the AED 100 could instead be activated by the operator opening the lid 104, or by another operator-initiated action. Such single-action methods and systems for activating medical devices are described in more detail in U.S. application Ser. No. 10/139,942, filed May 6, 2002, entitled "Single-Action Method of Activating and Exposing User Interface of Medical Device," and specifically incorporated herein by reference. Activation of the medical device by any of these or other methods or systems may be referred to in the context of the present invention as an "activation layer" of the layered user interface. On/off actuator 108 and lid 104 are examples of activators or activation devices that may be used by an operator to activate a medical device. Further, the size and color of on/off actuator 108 are examples of activation instructions concerning operator use of the activator or activation device. Moreover, the size and color of on/off actuator 108 is an indicator of provided by the housing, e.g., case, directing an operator to perform a sequence of operations that includes activating the defibrillator.

FIG. 3 illustrates the AED 100 of FIG. 1 when the lid 104 is opened, bringing the operator to the next layer of user interface component that is appropriate for use at this point in the operation of the device and the treatment of the patient, i.e., opening the lid 104 brings the operator to an electrode package 120 positioned within the housing 102 beneath the lid 104 and not held against a lower surface 138 of the lid 104. In one embodiment, the electrode package 120 is a bag attached to the housing 102 by an anchor pin 122. Contained within the electrode package 120 are a pair of defibrillation electrodes (not shown in FIG. 3) that are electrically coupled with monitoring and defibrillation circuitry inside the housing 102 by an electrode connector 124 and electrode wires 126.

As will be appreciated by those skilled in the defibrillator arts, once an AED is activated, the next step in its operation is typically to apply a pair of defibrillation electrodes to the patient's chest that are used to monitor the patient's heart rhythm and deliver a defibrillation pulse if necessary. Accordingly, in one embodiment of the present invention, the electrode package 120 is positioned beneath the lid 104 and sized so as to attract the operator's immediate attention as the next appropriate action to take in the operation of the device and treatment of the patient. To further intuitively guide the operator in the correct operation and application of the electrodes, the electrode package 120 includes a package opening member, such as handle 128, which the operator pulls to open the electrode package along a tear line 130 and release the defibrillation electrodes packaged therein. To further bring attention to the handle, the handle is configured and colored to be conspicuous to the operator. For example, in one embodiment the handle 128 is large in size (relative to its required mechanical function) and colored bright red to visually contrast with the substantially white colored electrode package 120. Also, the handle has a skew orientation—i.e., not aligned parallel with the sides of the substantially rectangular electrode package 120—which further visually attracts the operator's attention, Still further, the handle 128 itself may include diagrammatic arrows 134 indicating the direction the operator should pull the handle and the upper surface of the electrode package 120 may include a graphical diagram 132 depicting how the operator should grasp and pull the handle 128 in order to open the electrode package 120 (as well as a patient diagram 136 that depicts the appropriate placement of the defibrillation electrodes on the chest of a patient). As shown in FIG. 3, graphical diagram 132 may be visible through an opening of handle 128. The operator may place one or more fingers through the opening handle 128. For example, as shown in FIG. 3, graphic diagram 132 depicts that the operator may slip at least one finger, and more likely more fingers, through the opening to pull handle 128.

In addition to the size, configuration, color and placement of the electrode package 120 and the handle 128, the AED 100 may issue audible instructions to the operator upon opening of the lid 104 to pull the handle 128 to open the electrode package 120, as well as audible instructions to first call for help and remove clothing from the patient's chest. It will be appreciated by those skilled in the art that although highly desirable, such audible instructions may be omitted without departing from the spirit and scope of the present invention. The size, shape and color of electrode package 120 and handle 128, as well as graphical diagram 132, diagrammatic arrows 134, patient diagram 136 and audible instructions, are examples of connection instructions concerning operator use of a connector, e.g., the defibrillation electrodes. Additionally, the size, shape and color of the electrode package and handle, as well as the graphical diagram and diagrammatic arrows, are examples of indicators of an electrode package that direct an operator to perform a sequence of operations that includes opening the electrode package.

Figure 4:
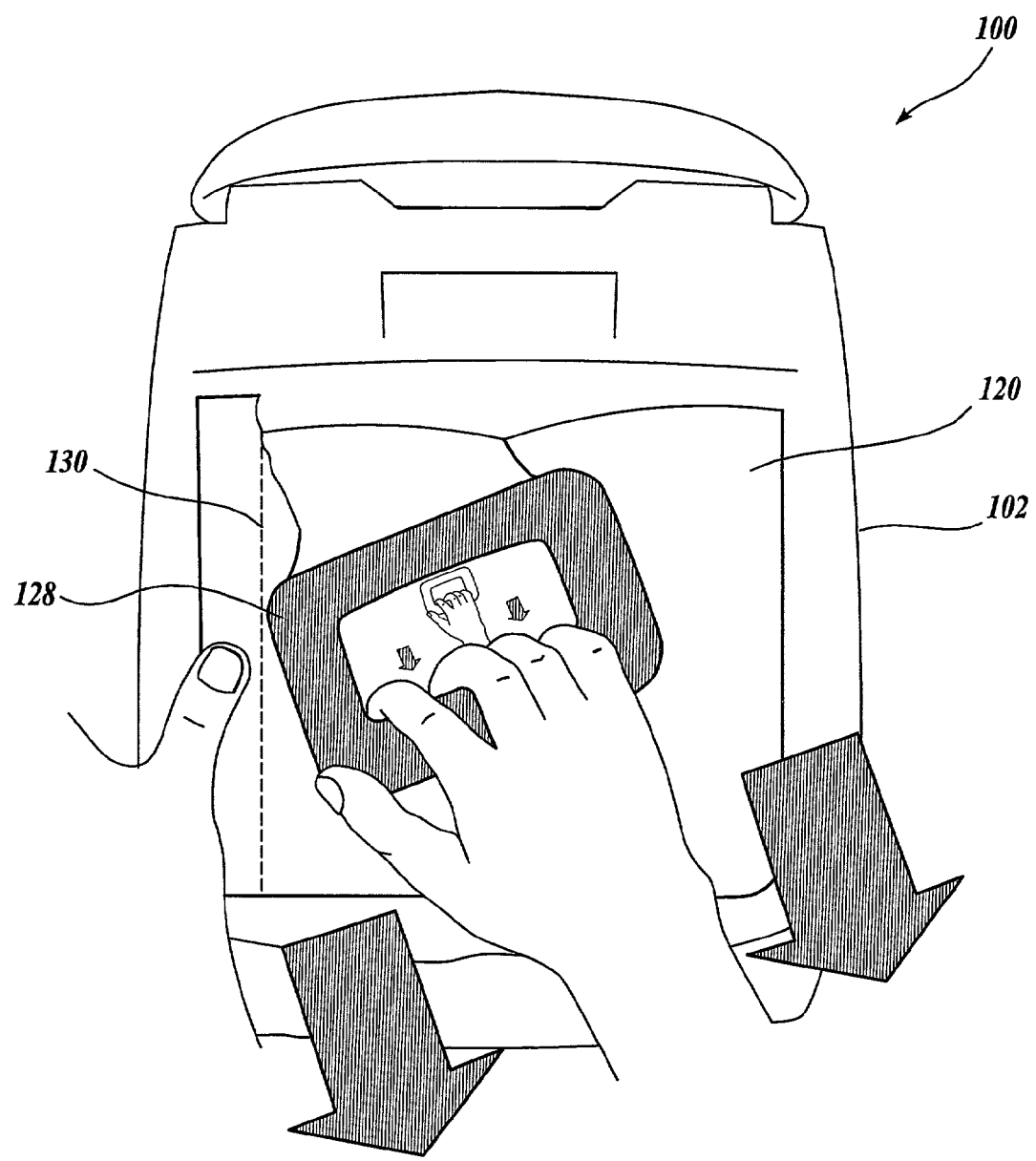
FIG. 4 depicts an operator of the defibrillator opening the electrode package by grasping and pulling the handle.
Figure 5:
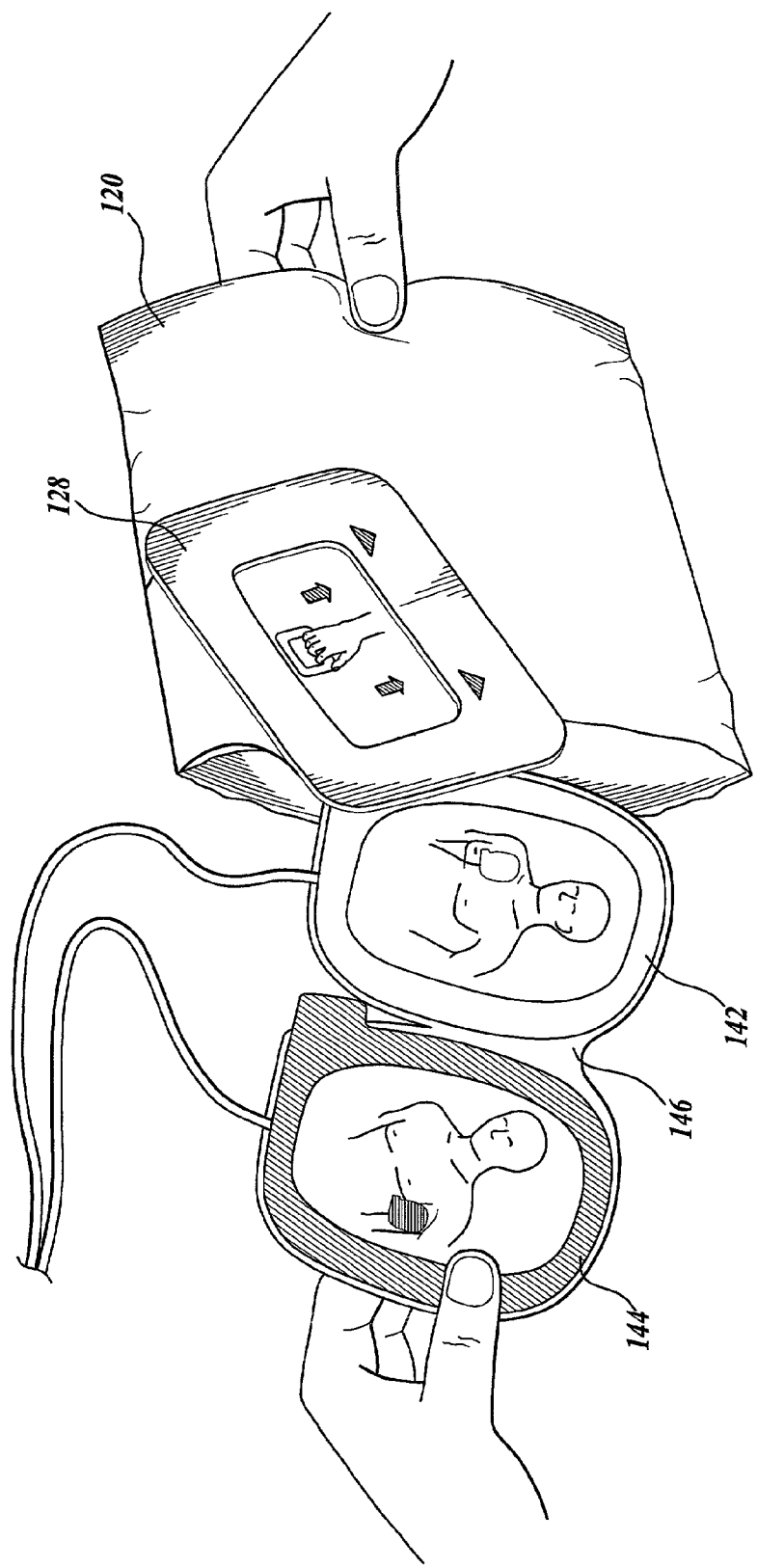
FIG. 5 depicts the operator removing defibrillation electrodes from the opened electrode package.
Figure 6:
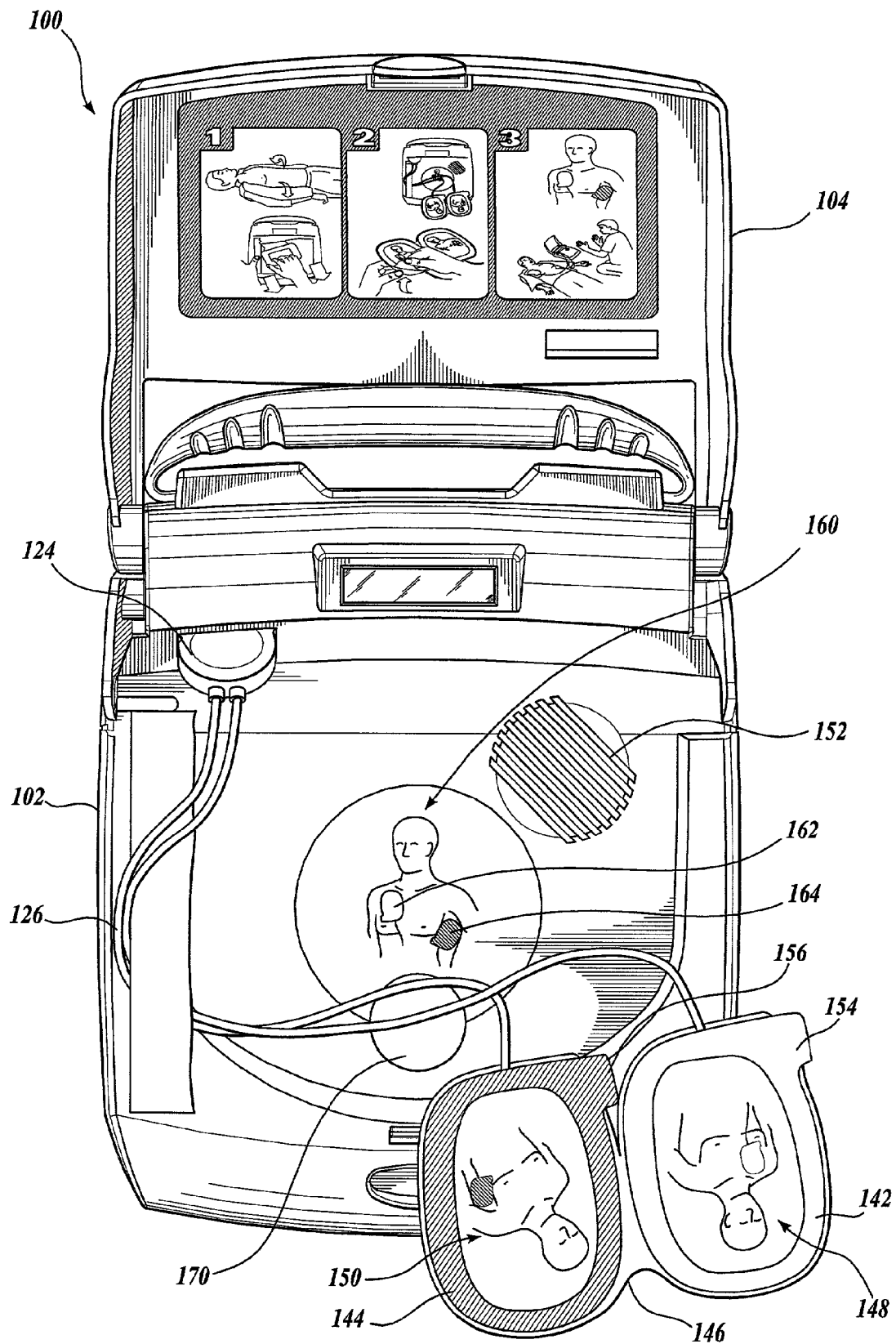
FIG. 6 depicts the defibrillator after the defibrillation electrodes have been removed from the electrode package, now discarded.
Figure 7:
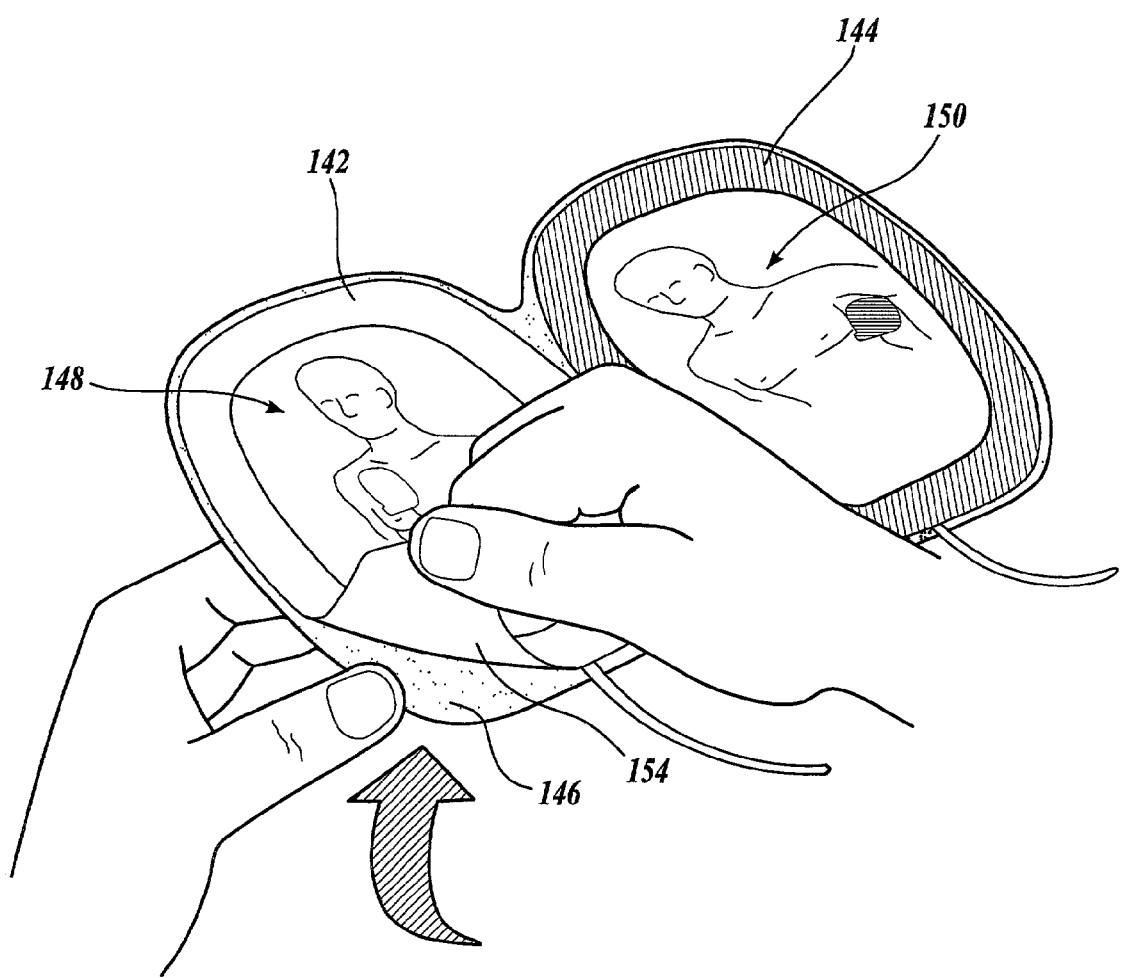
FIG. 7 depicts the operator removing an electrode pad from a liner sheet on which the defibrillation electrodes are removably adhered.

FIG. 4 depicts the operator pulling on the handle 128 in order to open the electrode package 120 along the tear line 130. FIG. 5 then shows the operator removing the defibrillation electrodes 142, 144 (also commonly referred to as electrode pads) from the electrode package 120. Referring now to FIG. 6, the AED 100 is shown after the defibrillation electrodes 142, 144 have been removed from the opened electrode package 120 (which the operator has discarded or otherwise set aside, and is not shown in FIG. 6). The operator is now presented with the next layer of user interface component, namely, the defibrillation electrodes 142, 144 themselves. As indicated above, defibrillation electrodes 142, 144 are an example of a connector that may be used by an operator to connect a medical device to a patient. In the embodiment shown in FIG. 7, the defibrillation electrodes 142, 144 are positioned on a single pad liner 146 of contrasting color to that of the electrodes. (Those skilled in the art will appreciate that the defibrillation electrodes could instead be positioned on separate liners or in other suitable configurations.) For example, the defibrillation electrodes 142 and 144 may have respectively colored boundaries of yellow and red, with the liner 146 being blue-colored plastic. It has been found that lay persons unfamiliar with the use of AEDs or medical devices often do not realize that defibrillation electrodes include a layer of gel covered by a liner that must be removed in order to reveal the gel and affix the electrode to the patient. The different colors of the electrodes and the liner, along with the disposition of the defibrillation electrodes 142, 144 together on a single liner 146, intuitively emphasize to the operator that the defibrillation electrodes must be separated from one another and from the liner in order to be applied.

To further guide the operator in releasing the liner from the electrodes, each of the defibrillation electrodes 142 and 144 has a respective one of tabs 154 and 156 (see also FIG. 6), which the operator grasps and pulls in order to remove the defibrillation electrodes from the liner 146. The tabs 154, 156 may include diagrammatic arrows that visually indicate to the operator to pull the tabs. In addition, the tabs 154, 156 are large and protrude beyond the boundary of the liner 146, so as to be visually obvious to the operator.

To further guide the operator in the placement of the electrodes once separated from one another and removed from the liner 146, the defibrillation electrodes 142 and 144 include pad placement diagrams 148 and 150, respectively, which illustrate for the operator the proper location for each electrode on the patient. In one embodiment, each pad placement diagram depicts the proper location of only its corresponding pad, it does not depict both pads. Proper placement of each electrode is further intuitively encouraged by placing the defibrillator electrode 142 intended for placement on the left side of the patient (from the operator's perspective) on the left side of the liner 146, and placing the defibrillator electrode 144 intended for placement of the right side of the patient on the right side of the liner 146. Proper placement is encouraged further by coloring the boundaries of the defibrillation electrodes 142 and 144 differently (e.g., yellow and red as mentioned above) and by using corresponding colors in the pad placement diagrams 148 and 150.

In addition to the size, configuration, color and placement of the defibrillation electrodes 142 and 144 and the liner 146, the AED 100 may issue additional audible instructions to the operator via an audio speaker 152 to remove each of the defibrillation electrodes 142, 144 from the liner 146 and to then apply the defibrillation electrodes to the exposed chest of the patient. It will be appreciated by those skilled in the art that although highly desirable, such audible instructions may be omitted without departing from the spirit and scope of the present invention. The sizes, shapes, colors and arrangement of defibrillator electrodes 142 and 144, liner 146, and tabs 154 and 156, as well as diagrammatic arrows, placement diagrams 148 and 150 and audible instructions, are examples of connection instructions concerning operator use of a connector, e.g., the defibrillation electrodes. Further, the sizes, shapes, colors and arrangement of the defibrillator electrodes, liner, and tabs, as well as the diagrammatic arrows and placement diagrams, are examples of indicators of the defibrillation electrodes that direct an operator through a sequence of operations that includes placing the electrodes on a patient.

Figure 8:
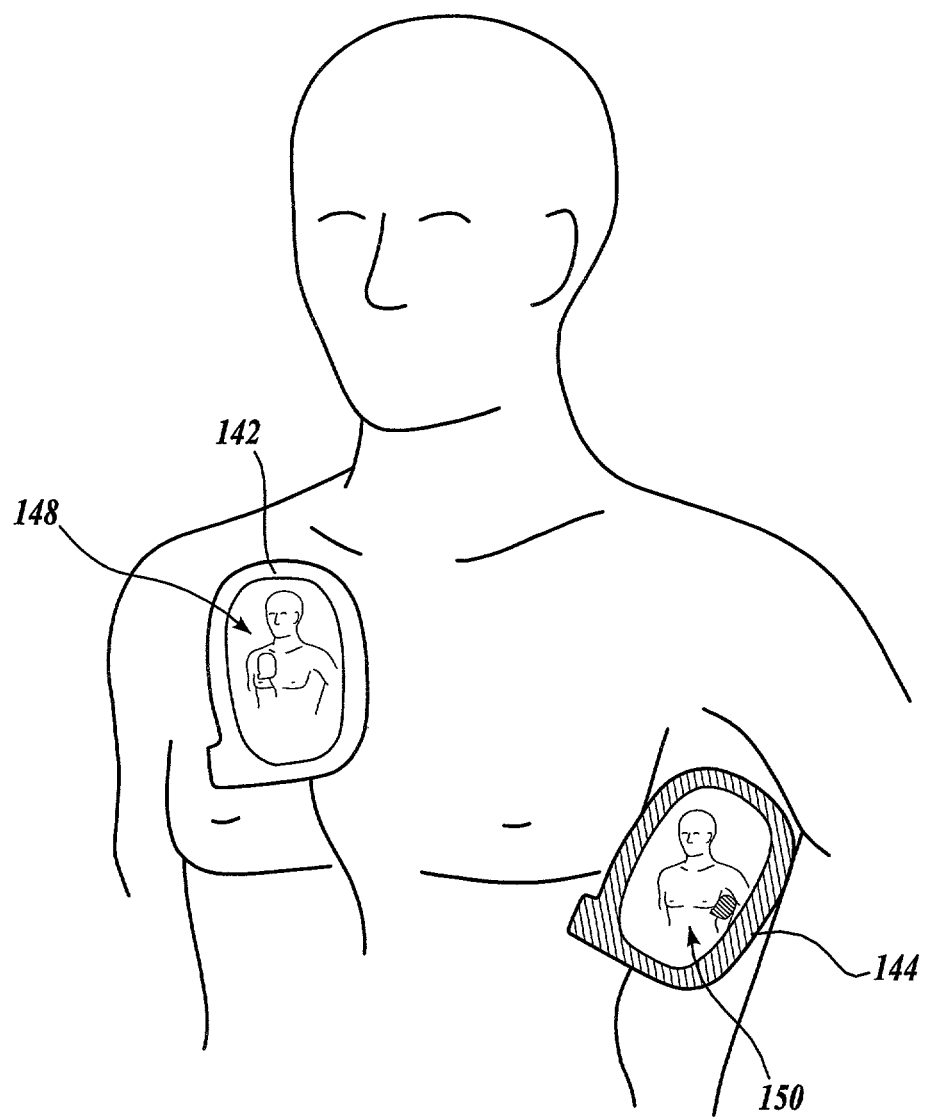
FIG. 8 depicts proper placement of the defibrillation electrodes on the exposed chest of a patient.

FIG. 8 depicts the proper placement of the defibrillation electrodes 142, 144 on the exposed chest of the patient, consistent with the colors of the defibrillation electrodes, the positioning of the defibrillation electrodes on the liner, the pad placement diagrams 148, 150 on the defibrillation electrodes, and the audible instructions. The deployment of the electrode package 120 and the defibrillation electrodes 142, 144 as, for example, described above, may be referred to in the context of the present invention as an "electrode application layer" of the layered user interface.

Returning to FIG. 6, once the electrode package 120 is removed from the AED 100, the next layer of user interface component made available to the operator is the shock key 170 and an electrode status display 160 that depicts the proper positioning of the defibrillation electrodes 142, 144 on the patient. As will be appreciated from the description below, this layer of user interface component intuitively directs the user to what may become the next appropriate action in the operation of the device and treatment of the patient, namely, depressing the shock key 170 to initiate delivery of a defibrillation pulse to the patient if the electrodes are properly attached and the device detects the presence of a shockable heart rhythm. Shock key 170 is an example of an initiator that may be used by an operator to initiate treatment of the patient by a medical device.

Returning to the electrode status display 160, the diagram includes electrode indicators 162, 164 that indicate whether the defibrillation electrodes have been placed on the patient. The electrode indicators 162, 164 can include visual display elements, such as light-emitting diodes, that produce first and second visual signals. For example, the electrode indicators 162 and 164 will display a red light if one of the defibrillation electrodes 142 and 144 has not yet been or is not attached to the patient. Conversely, once the corresponding defibrillation electrode is properly placed on the patient (i.e., the liner has been removed, the electrode attached to the bare-chested patient, and impedance has been detected), the electrode indicators 162, 164 then display a green light.

Figure 9:
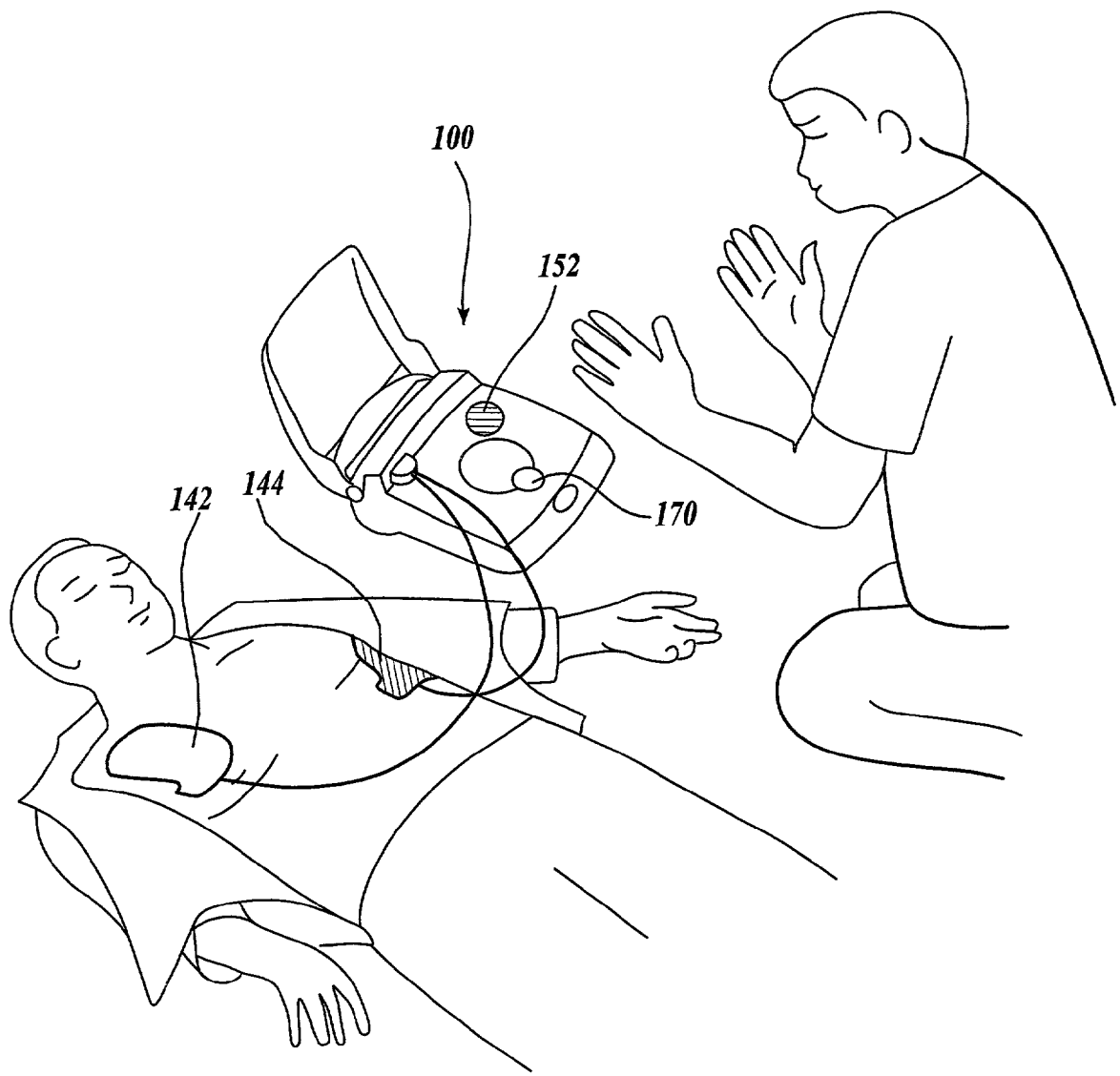
FIG. 9 depicts the defibrillator shown in FIG. 1 while in use by an operator.

Once the electrodes are properly placed on the patient, the AED 100 begins collecting electrocardiogram ("ECG") signals from the patient and analyzing them for a shockable rhythm. FIG. 9 depicts the operator awaiting further device operation and/or treatment instructions from the AED 100. During this time, the AED 100 may issue additional instructions, such as instructions to check the firm adhesion of defibrillation electrodes 142, 144 to the patient, CPR instructions, emergency notification instructions, etc.

If a shockable rhythm is detected, the operator's attention is immediately drawn to the shock key 170 (which is only made available to the operator after the electrode package 120 has been opened and removed from the housing 102) via further visual and/or audible indications. For example, the shock key 170 may be sized, colored and labeled such that it draws the attention of the operator and indicates its function to the operator. For example, the shock key 170 shown in FIG. 6 is prominently sized, centrally placed, contrastingly colored (e.g., red), and includes a diagram depicting an electric shock delivered to a heart. When a shockable rhythm is detected, the shock key 170 may also flash or issue some other suitable visual signal so as to indicate to the operator that he or she can depress the shock key 170 to initiate delivery of a defibrillation pulse to the patient. Additionally, the AED 100 may issue audible instructions to the operator via the audio speaker 152 to depress the shock key 170. Accordingly, it can be appreciated from the above description, that the operator is automatically and intuitively guided by the layered user interface of the present invention from the on/off actuator 108 to the shock key 170, to ultimately initiate delivery of a defibrillation pulse to the patient.

Figure 10:
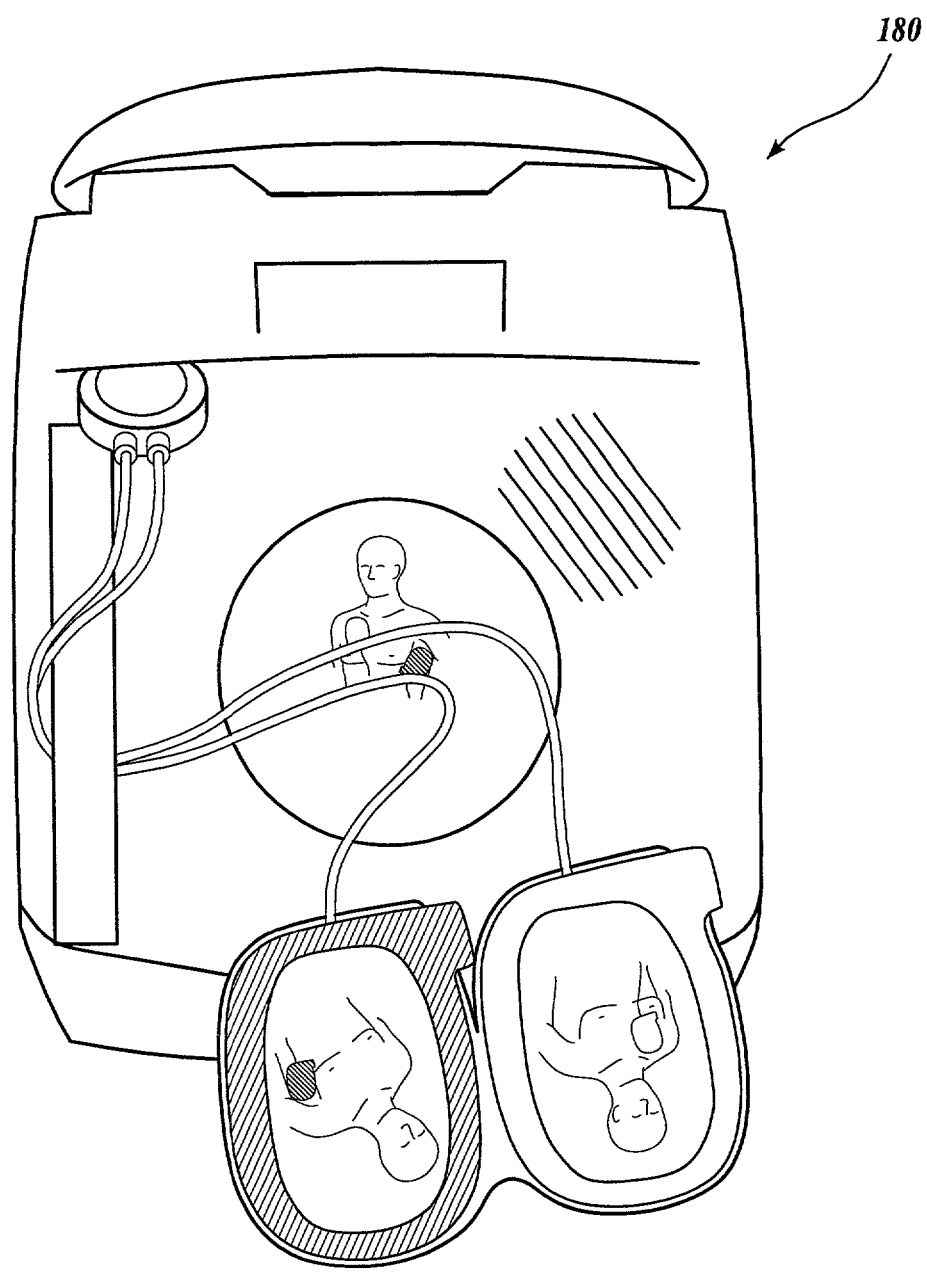
FIG. 10 depicts a fully automatic defibrillator.

It will be appreciated, however, that in another embodiment of the present invention, the AED 100 can be a fully automatic defibrillator (rather than a semiautomatic defibrillator), meaning that the device automatically initiates delivery of a defibrillation pulse to a patient upon detecting a shockable heart rhythm. Accordingly, operator initiation is not required and the shock key 170 is eliminated. A fully automatic AED 180 is shown in FIG. 10, in which no shock key is provided, and in which the AED itself initiates delivery of the defibrillation pulse. The visual and/or audible instructions provided to guide the operator through the delivery of the defibrillation pulse, as well as the shock key 170 if the AED is semiautomatic, may be referred to in the context of the present invention as a "defibrillation pulse delivery layer" of the layered user interface.

Figure 11:
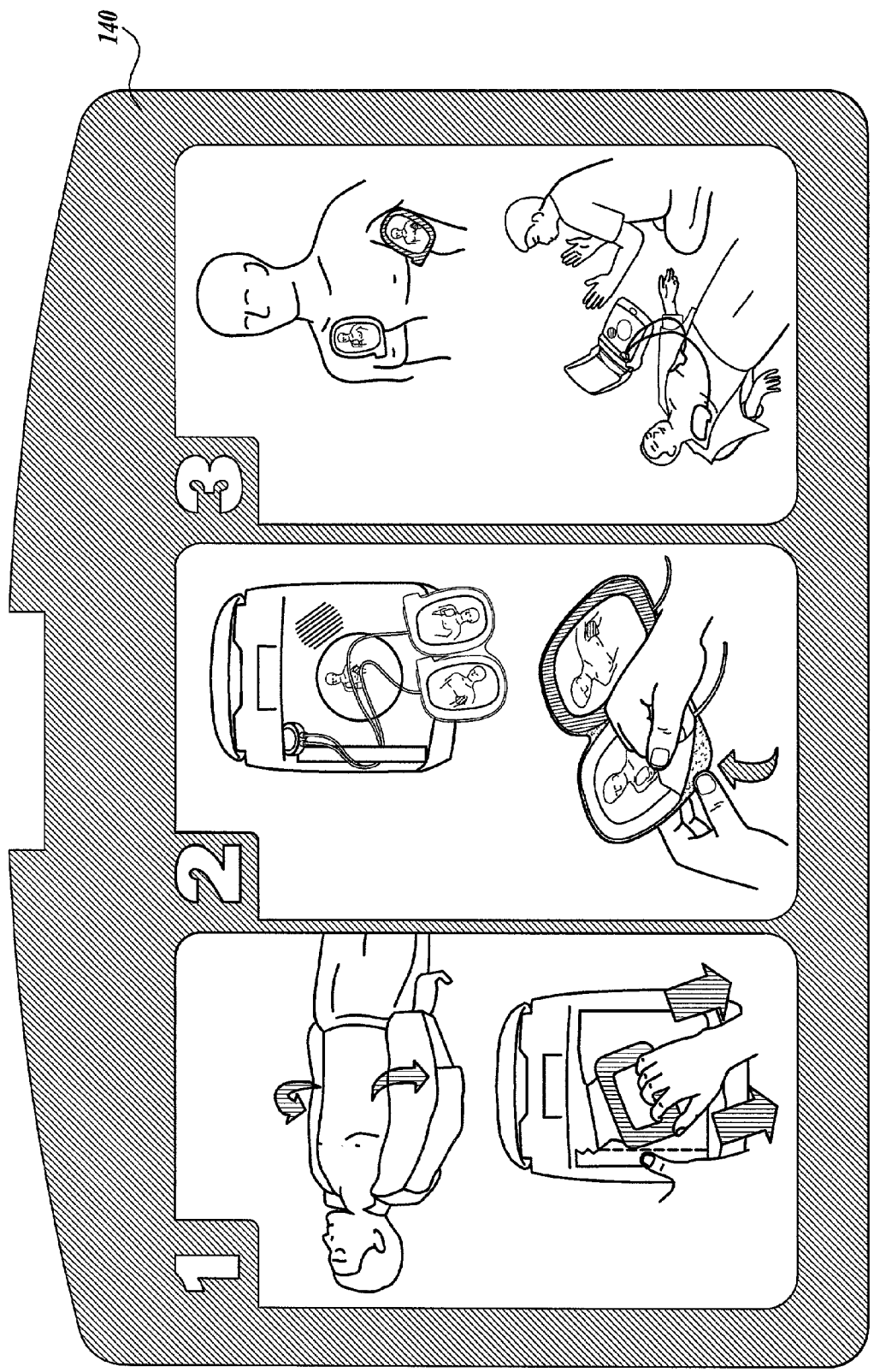
FIG. 11 depicts a reference card mounted on a surface portion of the defibrillator lid made visible to the operator when the lid is opened.

Returning to FIG. 3, given the difficulty a lay person may have opening the electrode package 120, applying the defibrillation electrodes to the patient and operating the AED, the AED 100 may also include another layer of user interface component that is made available to the operator simultaneously with the electrode package 120 when the lid 104 is opened. More specifically, a reference card 140 may be mounted to a bottom surface 138 of the lid 104 that graphically depicts a sequence of the basic instructions to be followed by the operator during use of the AED. FIG. 11 shows a close-up view of the reference card 140. The illustrated embodiment of the reference card 140 depicts the following basic instructions: (1) remove the patient's clothing and pull the handle on the electrode package; (2) remove the electrodes from the package and peel them off the liner; and (3) apply the electrodes to the patient's chest, stand clear and follow the prompts (visual and/or aural) issued by the AED. Accordingly, the operator is given an immediate and always visible idea of what steps must be taken to operate the device and treat the patient, including connection instructions concerning operator use of a connector, e.g., defibrillation electrodes. Those skilled in the art will appreciate, however, that the reference card 140 may include any instructions, diagrams, text, etc, deemed desirable by the manufacturer.

In one embodiment of the present invention, the operator is further guided through the layered user interface in the operation of the device and treatment of the patient by a series of audible instructions or voice prompts provided by the AED 100 to the operator via an audio speaker 152 (see FIG. 6), along with electrically driven visual signals, such as the electrode indicators 162, 164 and flashing shock key 170. One skilled in the art will understand that any of a wide variety of combinations of hardware circuitry and software programming can be used to detect or otherwise time the sequence of operator actions and then provide the corresponding signals to the audio speaker 152 and driven visual elements. Particular details of such circuitry and software need not be disclosed for one skilled in the art to understand the teachings of the present invention. However, one example of such circuitry and software as implemented in an AED is described in commonly assigned U.S. Pat. No. 6,334,070, entitled "Visual and Aural User Interface for an Automated External Defibrillator," issued Dec. 25, 2001, and specifically incorporated herein by reference.

Referring to FIG. 12, a flow diagram is presented to depict the sequence of audible and electrically driven visual instructions issued by the AED 100 for the scenario in which a defibrillation shock is actually delivered. A prompting routine 200 is executed by the AED 100, and includes issuing audible instructions via the audio speaker 152 and electrically driven visual instructions via the electrode indicators 162, 164 and flashing shock key 170. By executing prompting routine 200, AED 100 may provide a prompting system for prompting an operator with instructions, such as the example audible and visual instructions described below.

The routine 200 begins in a decision block 210 testing whether the AED 100 has been activated. Once the condition of block 210 is met, the routine 200 continues to block 220, in which the AED 100 issues audible instructions to the operator concerning calling for help, removing clothing to expose the patient's chest, and opening the electrode package 120. The routine 200 continues with a decision block 230 testing whether the electrode package 120 has been opened. If not, the routine 200 returns to block 220.

Once the condition of decision block 230 is met, the routine 200 then continues to block 240, in which the AED 100 issues audible instructions concerning removal of the defibrillation electrodes 142, 144 from the electrode package 120 and removal of the electrodes from the liner 146. The routine 200 then continues to a decision block 250 testing whether the defibrillation electrodes 142, 144 have been removed from the liner 146. If not, the routine 200 returns to block 240 and the appropriate audible instructions are repeated.

Once the condition of decision block 250 is met, the routine 200 then continues with a third instructional step 260, in which the AED 100 issues audible instructions concerning placement of the defibrillation electrodes 142, 144 on the patient's chest and lights up the LEDs 162, 164 of the electrode status display 160 accordingly. The routine 200 continues to a decision block 270 and tests whether the defibrillation electrodes 142, 144 have been properly placed on the patient. If not, the routine 200 returns to block 260 to repeat the appropriate visual and aural instructions to the operator.

Once the condition of decision block 270 is met, the routine 200 continues to block 280, in which the AED 100 issues visual information confirming the proper placement of the defibrillation electrodes 142, 144 (i.e., lights the LEDs of the electrode status display 160 green) and audible information concerning evaluation of the patient's heart rhythm and preparations for delivering a defibrillation pulse. The AED 100 then issues visual instructions (e.g., flashing shock key 170) and audible instructions to the operator to press the shock key 170 and initiate delivery of the defibrillation pulse to the patient.

Those skilled in the art will appreciate that a number of well-known operations are not presented in the flow diagram of FIG. 12, such as instructions relating to patient movement (if detected), decisions by the AED diagnostic circuitry not to shock, instructions relating to CPR, and the like. Such AED operations are described in U.S. Pat. No. 6,334,070, already incorporated herein by reference. Those skilled in the art will further appreciate that various operations can be omitted from the flow diagram of FIG. 12 and performed and/or input by an operator or other device, or substituted with a time-out function without departing from the spirit and scope of the present invention.

While certain embodiments of the invention have been illustrated and described, those skilled in the art will appreciate that various changes can be made without departing from the spirit and scope of the invention. Additional layers of user interface components may be added as appropriate to assist in the operation of the device, treatment of the patient or perhaps the maintenance of the device. For example, as illustrated in FIGS. 1 and 3, the AED 100 may include a readiness display 110 that includes various symbols indicating the status of the AED, such as indicating its readiness for use, the need to replace a battery unit, the need for inspection or repair, or other indication as would be understood by those skilled in the art. The AED 100 may also include a window 112 in the lid 104 through which an electrode expiration date 114 stamped on the upper surface of the electrode package 120 (see FIG. 3) can be seen by the operator when the lid is closed. Together these components may be referred to in the context of the present invention as a "status layer" of the user interface.

We claim:

1. An external defibrillator comprising:
   a housing;
   a lid coupled to the housing, the lid movable between a closed position in which the lid covers at least a portion of a surface of the housing and an open position;
   an electrode package located over the surface of the housing and beneath the lid when the lid is in the closed position, wherein the electrode package remains in its position over the surface of the housing while the lid is moved into the open position and when the lid is in the open position until the electrode package is removed from its position over surface of the housing by an operator, and wherein the electrode package is not held against a lower surface of the lid, the electrode package including a handle comprising an opening and actuatable by the operator by slipping at least one finger through the opening to open the electrode package; and
   an initiator useable by the operator to initiate delivery of therapy to a patient by the defibrillator, the initiator located on the surface of the housing, wherein the initiator is located beneath the electrode package when the electrode package remains in its position over the surface of the housing when the lid is in the open position,
   wherein the electrode package becomes accessible by the operator upon moving the lid into the open position, and the initiator is accessible by the operator only upon removing the electrode package from its position over the surface of the housing.

2. The external defibrillator of claim 1, wherein movement of the lid to the open position activates the defibrillator.

3. The external defibrillator of claim 1, further comprising an actuator actuatable by the operator to release the lid for movement to the open position.

4. The external defibrillator of claim 3, wherein actuation of the actuator activates the external defibrillator.

5. The external defibrillator of claim 3, wherein the actuator comprises instructions concerning operator activation of the defibrillator.

6. The external defibrillator of claim 1, wherein the lid comprises instructions concerning operator activation of the defibrillator.

7. The external defibrillator of claim 1, wherein the initiator comprises a shock key actuatable by the operator to initiate delivery of the defibrillation pulse.

8. The external defibrillator of claim 1, wherein the initiator includes instructions for operation of the initiator to initiate delivery of therapy.

9. The external defibrillator of claim 1, wherein the electrode package contains the electrodes, and includes instructions for opening the package and for applying the electrodes to the patient.

10. The external defibrillator of claim 9, wherein the electrode package includes first instructions for opening the electrode package, and the electrodes within the package include second instructions for placing the electrodes on the patient.

11. The external defibrillator of claim 10, wherein the first instructions includes a diagram depicting pulling the handle to open the electrode package.

12. The external defibrillator of claim 10, wherein second instructions further comprise instructions that direct the operator to remove the defibrillation electrodes from a liner.

13. The external defibrillator of claim 9, wherein the electrodes have a color and are located on a single pad liner that has a different color.

14. The external defibrillator of claim 1,
    wherein the electrode package has sides that define a substantially rectangular shape, and
    wherein the handle is connected to the electrode package in a substantially non-parallel orientation with the sides of the electrode package.

15. The external defibrillator of claim 1,
    wherein electrode package contains a plurality of electrodes,
    the external defibrillator further comprising an electrode status display on the surface of the housing beneath the electrode package, and
    wherein the electrode status display includes electrode indicators that produce visual signals to indicate to the operator whether the electrodes are adequately attached to a patient for at least one of monitoring or delivery of therapy.

16. The external defibrillator of claim 1, in which the electrode package includes a diagram that indicates to the operator to slip at least one finger through the opening of the handle to open the electrode package.

17. The external defibrillator of claim 16, in which the diagram is positioned on the electrode package to be visible through the opening of the handle.

18. The external defibrillator of claim 1, in which the electrode package is located on the surface of the housing when the lid is in the closed position, and remains in its position on the surface of the housing while the lid is moved into the open position and when the lid is in the open position until the electrode package is removed from its position on the surface of the housing by the operator.

19. The external defibrillator of claim 1, in which the electrode package is attached to the surface of the housing.

20. An external defibrillator comprising:
    a housing;
    a lid coupled to the housing, the lid movable between a closed position in which the lid covers at least a portion of a surface of the housing and an open position;
    means for connecting the defibrillator to the patient located over the surface of the housing and beneath the lid when the lid is in the closed position, wherein the means for connecting the defibrillator remains in its position over the surface of the housing while the lid is moved into the open position and when the lid is in the open position until the means for connecting the defibrillator is removed from its position over the surface of the housing by an operator, wherein the means for connecting the defibrillator is contained within a package that includes a handle that has an opening, the handle actuatable by the operator by slipping at least one finger through the opening to open the package and access the means for connecting the defibrillator, and wherein the means for connecting the defibrillator is not held against a lower surface of the lid; and
    means useable by the operator for initiating delivery of therapy to a patient by the defibrillator, the initiating means located on the surface of the housing, wherein the initiating means is located beneath the electrode package when the connecting means remains in its position over the surface of the housing when the lid is in the open position,
    wherein the connecting means becomes accessible by the operator upon moving the lid into the open position, and the initiating means is accessible by the operator only upon removing the connecting means from its position over the surface of the housing.

21. The external defibrillator of claim 20, wherein the connecting means comprises instructions for directing operator use of the connecting means and the initiating means comprises instructions for directing operator use of the initiating means.

22. The external defibrillator of claim 20, further comprising means for indicating the status of the connecting means located beneath the connecting means, wherein the status indicating means becomes accessible by the operator only upon removing the connecting means from its position over the surface.

23. The external defibrillator of claim 20, in which the package includes a diagram that indicates to the operator to slip at least one finger through then opening of the handle to open the package.

24. The external defibrillator of claim 23, in which the diagram is positioned on the package to be visible through the opening of the handle.

25. The external defibrillator of claim 20, in which the means for connecting is located on the surface of the housing when the lid is in the closed position, and remains in its position on the surface of the housing while the lid is moved into the open position and when the lid is in the open position until the means for connecting is removed from its position on the surface of the housing by the operator.

26. The external defibrillator of claim 20, in which the means for connecting is contained within a package that is attached to the surface of the housing.

* * * * *

UNITED STATES PATENT AND TRADEMARK OFFICE
CERTIFICATE OF CORRECTION

PATENT NO. : 8,527,044 B2  Page 1 of 1
APPLICATION NO. : 10/147241
DATED : September 3, 2013
INVENTOR(S) : D. Craig Edwards et al.

It is certified that error appears in the above-identified patent and that said Letters Patent is hereby corrected as shown below:

In the Specification
In column 5, line 40, replace "indicator of provided" with -- indicated provided --;
In column 6, line 13, replace "attention," with -- attention. --;
In column 6, line 23, replace "opening handle" with -- opening to pull handle --.

Signed and Sealed this
Eighth Day of March, 2016

Michelle K. Lee
*Director of the United States Patent and Trademark Office*